United States Patent [19]

Kämmerer et al.

[11] Patent Number: 5,714,514
[45] Date of Patent: Feb. 3, 1998

[54] 2-CYANO-3-MERCAPTOCROTONAMIDES

[75] Inventors: Friedrich-Johannes Kämmerer, Hochheim; Rudolf Schleyerbach, Hofheim; Werner Thorwart, Hochheim, all of Germany

[73] Assignee: Hoechst Aktiegesellschaft, Frankfurt am Main, Germany

[21] Appl. No.: 715,270

[22] Filed: Sep. 16, 1996

[30] Foreign Application Priority Data

Sep. 19, 1995 [DE] Germany .................. 195 34 649.1

[51] Int. Cl.$^6$ .................. A61K 31/275; A61K 31/33; C07C 255/33
[52] U.S. Cl. .................. 514/526; 514/519; 558/392
[58] Field of Search .................. 558/392

[56] References Cited

PUBLICATIONS

M. Yokoyama et al., J. Org. Chem. 49, pp. 74–78 (1984).
K. Hartke, et al., Archiv der Pharmazie Bd. 301, No. 8, pp. 601–610 (1968).

*Primary Examiner*—Johann Richter
*Assistant Examiner*—Ebenezer Sackey
*Attorney, Agent, or Firm*—Finnegan, Henderson, Farabow, Garrett & Dunner, L.L.P.

[57] ABSTRACT

The present invention relates to 2-cyano-3-mercaptocrotonamide derivatives, a process for their preparation, and their use the treatment of immune disorders, carcinomatous disorders, rejection reactions in transplantations and skin disorders or allergy.

5 Claims, No Drawings

2-CYANO-3-MERCAPTOCROTONAMIDES

The invention relates to 2-cyano-3-mercaptocrotonamide derivatives, a process for their preparation, and use thereof as pharmaceuticals.

Some of the compounds which can be used according to the invention have already been described, but nothing is known about their use as pharmaceuticals (Hartke et al., Arch Pharm, (1968) 301 (8), pages 601–610; Yokoyama et al., J Org Chem, (1984) 49, pages 74–78).

SUMMARY OF THE INVENTION

The invention relates to a compound of the formula I

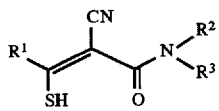
(I)

or a stereoisomeric form thereof, or a physiologically tolerable salt thereof, wherein
$R^1$ is
a) a hydrogen atom,
b) $(C_1-C_{17})$-alkyl,
c) $(C_1-C_4)$-alkyl, mono- or polysubstituted by fluorine, chlorine, bromine or iodine,
d) phenyl,
e) phenyl, mono- or polysubstituted by
 1) fluorine, chlorine, bromine or iodine,
 2) nitro,
 3) cyano,
 4) $(C_1-C_4)$-alkyl,
 5) $(C_1-C_4)$-alkyl, mono- or polysubstituted by fluorine, chlorine, bromine or iodine,
 6) $(C_1-C_4)$-alkoxy,
 7) $(C_1-C_4)$-alkoxy, mono- or polysubstituted by fluorine, chlorine, bromine or iodine,
f) benzyl,
g) $(C_3-C_7)$-cycloalkyl,
h) alkenyl having 2 or 3 carbon atoms or
i) alkynyl having 2 or 3 carbon atoms,
$R^2$ is
a) a hydrogen atom,
b) $(C_1-C_4)$-alkyl,
c) phenyl,
d) phenyl-$(C_1-C_2)$-alkyl or
e) alkenyl having 2 to 3 carbon atoms, or
$R^3$ is
a) a mono-, di- or trinuclear, unsaturated heterocyclic radical having 3 to 13 carbon atoms and 1 to 4 heteroatoms from the group consisting of oxygen, sulfur and nitrogen, of which at most one of the heteroatoms in the ring system is other than nitrogen, and is unsubstituted or mono- or polysubstituted by
 1) fluorine, chlorine, bromine or iodine,
 2) $(C_1-C_4)$-alkyl,
 3) $(C_{1-C4})$-alkyl, mono- or polysubstituted by fluorine, chlorine, bromine or iodine,
 4) $(C_1-C_4)$-alkoxy,
 5) $(C_1-C_4)$-alkoxy, mono- or polysubstituted by fluorine, chlorine, bromine or iodine,
 6) nitro,
 7) hydroxyl,
 8) carboxyl,
 9) carbamoyl or
 10) an oxo group,
b) a radical of the formula II

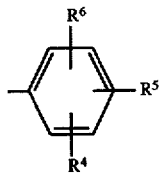
(II)

wherein $R^4$, $R^5$ and $R^6$ are each independently;
 1) a hydrogen atom,
 2) $(C_1-C_4)$-alkyl,
 3) $(C_1-C_4)$-alkyl, mono- or polysubstituted by fluorine, chlorine, bromine or iodine,
 4) in which $R^4$ is a hydrogen atom and $R^5$ and $R^6$, together with the phenyl ring of the formula II, form a naphthalene ring,
 5) in which $R^4$ is a hydrogen atom and $R^5$ and $R^6$ form a methylenedioxy radical,
 6) $(C_1-C_4)$-alkoxy,
 7) $(C_1-C_4)$-alkoxy, mono- or polysubstituted by fluorine, chlorine, bromine or iodine,
 8) $(C_1-C_4)$-alkylmercapto,
 9) $(C_1-C_4)$-alkylmercapto, mono- or polysubstituted by fluorine, chlorine, bromine or iodine,
 10) fluorine, chlorine, bromine or iodine,
 11) nitro,
 12) cyano,
 13) hydroxyl,
 14) carboxyl,
 15) $(C_1-C_4)$-alkylsulfonyl,
 16) carbalkoxy, having 1 to 3 carbon atoms in the alkyl chain,
 17) benzoyl,
 18) benzoyl, mono- or polysubstituted by
  18.1 fluorine, chlorine, bromine or iodine,
  18.2 $(C_1-C_4)$-alkyl or
  18.3 $(C_1-C_4)$-alkoxy,
 19) phenyl,
 20) phenyl, mono- or polysubstituted by
  20.1 $(C_1-C_4)$-alkoxy,
  20.2 fluorine, chlorine, bromine or iodine or
  20.3 $(C_1-C_4)$-alkyl,
 21) phenoxy, or
 22) phenoxy, mono- or polysubstituted by $(C_1-C_3)$-alkoxy, mono- or polysubstituted by
  22.1 fluorine, chlorine, bromine or iodine,
  22.2 $(C_1-C_3)$-alkyl, mono- or polysubstituted by fluorine, chlorine, bromine or iodine, or
  22.3 fluorine, chlorine, bromine or iodine,
c) a radical of the formula III

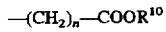
(III)

in which $R_{10}$ is
 1) a hydrogen atom or
 2) $(C_1-C_4)$-alkyl and
n is an integer from 1 to 12, or
d) $R^2$ and $R^3$, together with the nitrogen atom to which they are bonded, form a 4- to 7-membered ring, which is unsubstituted or substituted by carbonyl on the carbon atom adjacent to the nitrogen atom, or
e) $R^2$ and $R^3$, together with the nitrogen atom to which they are bonded, form a 5- to 6-membered ring of the formula IV

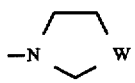

(IV)

wherein W is
1) —CH$_2$—,
2) —CH$_2$—CH$_2$—,
3) 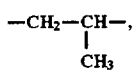

—CH$_2$—CH—,
      |
      CH$_3$

4)

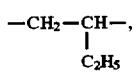

—CH$_2$—CH—,
      |
      C$_2$H$_5$

5)

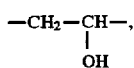

—CH$_2$—CH—,
      |
      OH

6) —CH$_2$—O— or
7) —CH$_2$—S—,
with the proviso that R$^2$ and R$^3$ are other than a hydrogen atom and R$^1$ is other than phenyl, ethyl or methyl.

A preferred compound of the formula I or a physiologically tolerable salt of the compound of the formula I, or a stereoisomeric form of the compound of the formula I wherein
R$^1$ is
  a) a hydrogen atom,
  b) (C$_1$–C$_6$)-alkyl,
  c) (C$_1$–C$_4$)-alkyl, mono- or polysubstituted by fluorine, chlorine, bromine or iodine,
  d) phenyl,
  e) alkenyl having 2 or 3 carbon atoms or
  f) (C$_3$–C$_4$)-cycloalkyl,
R$^2$ is
  a) a hydrogen atom,
  b) (C$_1$–C$_4$)-alkyl,
  c) benzyl or
  d) alkenyl having 2 to 3 carbon atoms,
R$^3$ is
  a) pyridyl, mono- or polysubstituted by
    1) a hydrogen atom,
    2) fluorine, chlorine, bromine or iodine,
    3) nitro,
    4) (C$_1$–C$_3$)-alkyl or
    5) (C$_1$–C$_3$)-alkoxy,
  b) a radical of the formula II in which R$^4$, R$^5$ and R$^6$ can be identical or different and are
    1) a hydrogen atom,
    2) (C$_1$–C$_3$)-alkyl,
    3) (C$_1$–C$_3$)-alkyl, mono- or polysubstituted by fluorine, chlorine, bromine or iodine,
    4) in which R$^4$ is a hydrogen atom and R$^5$ and R$^6$ form a methylenedioxy radical,
    5) (C$_1$–C$_3$)-alkoxy,
    6) (C$_1$–C$_3$)-alkoxy, mono- or polysubstituted by fluorine, chlorine, bromine or iodine,
    7) (C$_1$–C$_3$)-alkylmercapto,
    8) (C$_1$–C$_3$)-alkylmercapto, mono- or polysubstituted by fluorine, chlorine, bromine or iodine,
    9) fluorine, chlorine, bromine or iodine,
    10) nitro,
    11) cyano,
    12) (C$_1$–C$_3$)-alkylsulfonyl,
    13) benzoyl,
    14) benzoyl, mono- or polysubstituted by
      14.1 fluorine, chlorine, bromine or iodine,
      14.2 (C$_1$–C$_3$)-alkyl or
      14.3 (C$_1$–C$_3$)-alkoxy,
    15) phenoxy, or
    16) phenoxy, mono- or polysubstituted by
      16.1 (C$_1$–C$_3$)-alkoxy, mono- or polysubstituted by fluorine, chlorine, bromine or iodine,
      16.2 fluorine, chlorine, bromine or iodine,
      16.3 (C$_1$–C$_3$)-alkyl, mono- or polysubstituted by fluorine, chlorine, bromine or iodine,
  c) a radical of the formula III in which R$^{10}$ is
    1) a hydrogen atom,
    2) (C$_1$–C$_4$)-alkyl and
  n is an integer from 1 to 12, or
  d) R$^2$ and R$^3$, together with the nitrogen atom to which they are bonded, form a 4- to 7-membered ring which is substituted by carbonyl on the carbon atom adjacent to the nitrogen atom.

A particularly preferred compound of the formula I or a physiologically tolerable salt of the compound of the formula I or a stereoisomeric form of the compound of the formula I wherein
R$^1$ is (C$_1$–C$_6$)-alkyl,
R$^2$ is a hydrogen atom,
R$^3$ is
  a) pyridyl, mono- or polysubstituted by fluorine, chlorine, bromine or iodine, or
  b) a radical of the formula II in which R$^4$, R$^5$ and R$^6$ can be identical or different and are
    1) a hydrogen atom or
    2) (C$_1$–C$_3$)-alkyl,
    3) (C$_1$–C$_3$)-alkyl, mono- or polysubstituted by fluorine, chlorine, bromine or iodine,
    4) in which R$^4$ is a hydrogen atom and R$^5$ and R$^6$ form a methylenedioxy radical,
    5) (C$_1$–C$_3$)-alkoxy,
    6) (C$_1$–C$_3$)-alkoxy, mono- or polysubstituted by fluorine, chlorine, bromine or iodine,
    7) fluorine, chlorine, bromine or iodine,
    8) nitro,
    9) benzoyl,
    10) benzoyl, mono- or polysubstituted by
      10.1 fluorine, chlorine, bromine or iodine,
      10.2 (C$_1$–C$_3$)-alkyl or
      10.3 (C$_1$–C$_3$)-alkoxy,
    11) phenoxy or
    12) phenoxy, mono- or polysubstituted by
      12.1 (C$_1$–C$_3$)-alkoxy, mono- or polysubstituted by fluorine, chlorine, bromine or iodine,
      12.2 fluorine, chlorine, bromine or iodine or
      12.3 (C$_1$–C$_3$)-alkyl, mono- or polysubstituted by fluorine, chlorine, bromine or iodine.

Particularly preferred compounds are 2-cyano3-mercapto-N-(4-trifluoromethylphenyl)crotonamide and sodium 2-cyano-N-(4-trifluoromethylphenyl)-crotonamide-3-thiolate.

The term alkyl or alkoxy is understood as meaning radicals whose carbon chain can be straight-chain, branched or cyclic. Cyclic alkyl radicals are, for example, 3- to 7-membered monocycles such as cyclopropyl, cyclobutyl, cyclopentyl, cyclohexyl or cycloheptyl. The cyclic alkyl radicals further also include polycycles such as adamantane, twistane or diamantane radicals.

The expression "$R^2$ and $R^3$, together with the nitrogen atom to which they are bonded, form a 4- to 7-membered ring" includes, for example, radicals which are derived from azetidine, pyrrolidine, piperidine or azepine. The "mono-, di- or trinuclear, unsaturated heterocyclic radicals having 3 to 13 carbon atoms" include, for example, thienyl, pyridyl, pyrimidinyl, pyrazinyl, pyridazinyl, imidazolyl, thiazolyl, thiazolinyl, oxazolyl, thiadiazolyl, benzoxazolyl, benzimidazolyl, quinolyl, pyrazolyl, acridinyl, indolyl, tetrazolyl or indazolyl.

Suitable physiologically tolerable salts of the compound of the formula I are, for example, alkali metal, alkaline earth metal and ammonium salts, including those of organic ammonium bases.

The invention also relates to a process for the preparation of the compound of the formula I or a physiologically tolerable salt of the compound of the formula I or an optionally stereoisomeric form of the compound of the formula I, which comprises
a) reacting a cyanoacetamide of the formula V

in the presence of a basic compound with a dithiocarboxylic acid of the formula VI

where $R^1$, $R^2$ and $R^3$ have the meanings mentioned for the compound of the formula I and $R^7$ is $C_1$-$C_6$-alkyl, or
b) resolving a compound of the formula I prepared according to process a), which on account of its chemical structure occurs in enantiomeric forms, into the pure enantiomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary group, or
c) either isolating the compound of the formula I prepared according to process a) or b) in free form or, in the case of the presence of acidic or basic groups, optionally converting it into physiologically tolerable salts.

DETAILED DESCRIPTION OF THE INVENTION

The preparation of physiologically tolerable salts from compounds of the formula I, including their stereoisomeric forms, capable of salt formation is carried out in a manner known per se. With basic reagents such as hydroxides, carbonates, hydrogencarbonates, alkoxides and also ammonia or organic bases, for example trimethyl- or triethylamine, ethanolamine or alternatively basic amino acids, for example lysine, ornithine or arginine, the carboxylic acids form stable alkali metal, alkaline earth metal or optionally substituted ammonium salts. If the compound of the formula I has basic groups in the radical $R^3$, stable acid addition salts can also be prepared with strong acids. Possible acids for this are both inorganic and organic acids, such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethanesulfonic, acetic, oxalic, tartaric or trifluoroacetic acid.

The preparation and reaction of the compound of the formula I is expediently carried out in a dispersing agent or solvent which under the reaction conditions behaves indifferently toward the reaction components. Those which can be used for this are, for example, nitriles such as acetonitrile, ethers such as diethyl ether, tetrahydrofuran or dioxane and alcohols such as methanol, ethanol, propanol and isopropanol. Basic compounds which can be used in this connection are, for example, alkali metal hydrides, sodium or potassium alkoxides of lower alcohols, alkali metal amides, sodium or potassium carbonate or bicarbonate and alkali metal hydroxides. In a preferred embodiment, a cyanoacetamide of the formula V is thioacylated using an ethyl dithiocarboxylate of the formula VI in the presence of a sodium or potassium alkoxide. The solvent or diluent used in this case is the alcohol used for the preparation of the alkoxide. The cyanoacetamides of the formula V needed as starting substances are known or can be prepared analogously from cyanoacetic acid and the amines of the formula VII

in which $R^2$ and $R^3$ have the meanings indicated above. The preparation of the dithiocarboxylic acid esters of the formula VI is carried out by alkylating the dithiocarboxylic acids with alkyl halides or dialkyl sulfates.

The invention also relates to pharmaceuticals which comprise an efficacious content of at least one compound of the formula I

or of a physiologically tolerable salt of the compound of the formula I or an optionally stereoisomeric form of the compound of the formula I, where the radicals $R^1$, $R^2$ and $R^3$ are as defined in formula I, but the provisos are included, together with a pharmaceutically suitable and physiologically tolerable excipient, additive and/or other active compounds and auxiliaries.

On account of their pharmacological properties, the compounds according to the invention are outstandingly suitable for the treatment and prophylaxis of immune or autoimmune disorders, disorders with increased cell growth such as cancer or restenosis, rejection reactions in transplants, skin disorders from the group consisting of psoriasis, psoriasis vulgaris, psoriasis eruptiva, erythrodermic psoriasis, pustular psoriasis, dermatitis, atopic dermatitis, allergic dermatitis, photoallergic dermatitis, dermatitis medicamentosa and eczema, asthma, urticaria, rhinitis, uveitis, type II diabetes, liver fibrosis, cystic fibrosis, colitis or allergy.

The immune or autoimmune disorders include systemic lupus erythematosus, multiple sclerosis, rheumatoid arthritis, nephrotic syndrome, in particular glomerulonephritis, ulcerative colitis or juvenile diabetes.

The carcinomatous disorders include lung cancer, leukemia, ovarian cancer, sarcoma, Kaposi's sarcoma, meningioma, cancer of the bowel, lymph node cancer, glioblastoma, cancer of the prostate or skin cancer.

In the case of organ transplantations, rejection reactions of the organ recipient to the transplanted organ or rejection reactions of the transplanted organ to the recipient can occur (host-versus-graft reaction or graft-versus-host reaction).

Rejection reactions mean all reactions of the recipient's body or of the transplanted organ which finally lead to cell or tissue death of the transferred organ or adversely affect the functionability and viability of the transferred organ or the recipient. In particular, this means acute and also chronic rejection reactions.

The term organ is understood as meaning all organs or organ parts (even several) in mammals, in particular man, for example the kidney, heart, skin, liver, muscle, cornea, bone, bone marrow, lung, pancreas, intestine or stomach.

The invention further relates to the use of the compound of the formula I for the preparation of pharmaceuticals for the prophylaxis and therapy of immune or autoimmune disorders, diseases with increased cell growth such as cancer or restenosis, rejection reactions in transplantations, skin disorders from the group consisting of psoriasis, psoriasis vulgaris, psoriasis eruptiva, erythrodermic psoriasis, pustular psoriasis, dermatitis, atopic dermatitis, allergic dermatitis, photoallergic dermatitis, dermatitis medicamentosa and eczema, asthma, urticaria, rhinitis, uveitis, type II diabetes, liver fibrosis, cystic fibrosis, colitis or allergy.

The invention also relates to a process for the production of a pharmaceutical, which comprises bringing at least one compound of the formula I into a suitable administration form with a pharmaceutically suitable and physiologically tolerable excipient and, if appropriate, other suitable active compounds, additives or auxiliaries.

Suitable solid or pharmaceutical preparation forms are, for example, granules, powders, coated tablets, tablets, (micro)capsules, suppositories, syrups, juices, suspensions, emulsions, drops or injectable solutions and also preparations having protracted release of active compound, in whose preparation are used customary auxiliaries, such as excipients, disintegrants, binders, coating agents, swelling agents, gildants or lubricants, flavorings, sweeteners and solubilizers. Frequently used auxiliaries which may be mentioned are magnesium carbonate, titanium dioxide, lactose, mannitol and other sugars, talc, milk protein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

The pharmaceutical preparations are preferably prepared and administered in dose units, each unit comprising, as active constituent, a certain dose of the compound of the formula I according to the invention. In solid dose units such as tablets, capsules, coated tablets or suppositories, this dose can be up to approximately 1000 mg, but preferably approximately 50 to 300 mg, and in injection solutions in ampoule form up to approximately 300 mg, but preferably approximately 10 to 100 mg.

For the treatment of an adult patient approximately 70 kg in weight, depending on the efficacy of the compounds according to formula I, daily doses of approximately 20 mg to 1000 mg of active compound, preferably approximately 100 mg to 500 mg, are indicated. Under certain circumstances, however, higher or lower daily doses may also be appropriate. The administration of the daily dose can be effected either by single administration in the form of an individual dose unit or else of several smaller dose units and also by multiple administration of subdivided doses at specific intervals.

EXAMPLE 1

Preparation of 2-Cyano-3-mercapto-N-(4-trifluoromethylphenyl)crotonamide

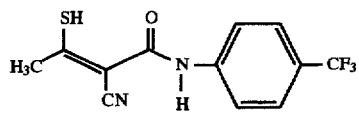

a) Preparation of N-(4-Trifluoromethylphenyl) cyanoacetamide.

Phosphorus pentachloride (83.3 g; 0.40 mol) is introduced into a solution of cyanoacetic acid (34.0 g; 0.40 mol) in 1.2 l of dichloromethane and the mixture is heated under reflux for 30 minutes. 4-Trifluoromethylaniline (41.0 g, 0.26 mol) is then introduced into said mixture within about 10 minutes and the reaction mixture is heated under reflux for 2 hours. After cooling to 20° C., the reaction mixture is treated with 500 ml of water and then stirred for 30 minutes. The aqueous phase is neutralized with sodium carbonate and the precipitate is filtered off with suction. The filter cake is washed with water and dried. 55.2 g of N-(4-trifluoromethylphenyl) cyanoacetamide are thus obtained in crystalline form. Melting point: 194°–195.5° C.

N-(4-Trifluoromethylphenyl)cyanoacetamide is prepared in a manner analogous to that described in GB 930.808.

b) Preparation of N-(4-Trifluoromethylphenyl) cyanoacetamide.

(9.1 g; 0.04 mol) is suspended in ethanol (150 ml) and treated at 0° C. to 5° C. with potassium tertiary butoxide (4.8 g; 0.04 mol). Ethyl dithioacetate (4.9 g; 0.04 mol) is then added dropwise with stirring at 15° C. to 20° C. The reaction mixture is heated to 70° C. to 75° C. After evolution of mercaptan is complete, the mixture is stirred for a further 30 minutes at 65° C. to 70° C. After cooling to room temperature, 100 ml of water are added dropwise to the reaction mixture and it is stirred for 15 minutes at room temperature. The reaction mixture is poured onto 400 ml of 0.1N hydrochloric acid and extracted 4 times by shaking with 100 ml of dichloromethane each time. The combined organic phases are washed twice with 300 ml of water each time, dried over sodium sulfate and concentrated to dryness under reduced pressure. The residue (10.5 g) is crystallized from 260 ml of ethanol. 5.6 g of 2-cyano-3-mercapto-N-(4-trifluoromethylphenyl)-crotonamide are thus obtained as yellowish crystals. Melting point: 183° C. to 184° C.

EXAMPLE 2

Prepation of Sodium 2-cyano-N-(4-trifluoromethylphenyl)crotonamide-3-thiolate

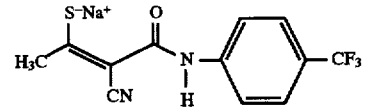

2-Cyano-3-mercapto-N-(4-trifluoromethylphenyl) crotonamide (2.6 g; 0.09 mol) from Example 1 is suspended in water (450 ml) and treated dropwise with stirring with a solution of sodium hydroxide (0.35 g; 0.009 mol) in water (10 ml) to 45° C. until the reaction mixture has a pH of 5.4. It is filtered and the filtrate is concentrated to dryness at 50° C. under reduced pressure. 3.0 g of sodium 2-cyano-N-(4-trifluoromethylphenyl)-crotonamide-3-thiolate are thus obtained as pale yellow crystals. Melting point: 235° C. to 240° C. (decomposition)

Pharmacological tests

1. Adjuvant-induced arthritis, modification according to Perper (Proc. Soc. exp. Biol. Med. 137, 506 (1971).

The experimental animals used are male rats of a Wistar-Lewis strain having a body weight of 130 to 200 g. On the 1st day the animals receive a subcutaneous injection in the tail of 0.1 ml of a Mycobacterium butyricum suspension (Difco; 6 mg/kg in liquid paraffin; Merck). The compounds to be compared are administered intraperitoneally twice daily from the 1st to the 12th day of the experiment; the determination as paw volume is then carried out on the 18th day.

Animals of a control group receive only the solvent. 6 animals are in each case used per dose and in the control group. The activity criterion used is the reduction of the increase in paw volume compared with the untreated control group. A dose of 25 mg of the compound according to Example 2 per kg of live weight of a Wistar-Lewis rat results in an 83% inhibition (38% inhibition at 12.6 mg/kg) of the increase in paw volume in comparison with an untreated control group.

What is claimed is:

1. A method of treating immune or autoimmune disorders, disorders with increased cell growth, rejection reactions in transplantations, skin disorders selected from the group consisting of psoriasis, psoriasis vulgaris, psoriasis eruptiva, erythrodermic psoriasis, pustular psoriasis, dermatitis, atopic dermatitis, allergic dermatitis, photoallergic dermatitis, dermatitis medicamentosa and eczema; and asthma, urticaria, rhinitis, uveitis, type II diabetes, liver fibrosis, cystic fibrosis, colitis or allergy, comprising administering to a patient an effective amount of a compound of the formula I

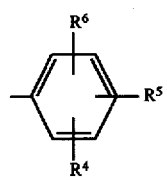

or a stereoisomeric form thereof, or a physiologically tolerable salt thereof, wherein $R^1$ is
a) a hydrogen atom,
b) $(C_1-C_{17})$-alkyl,
c) $(C_1-C_4)$-alkyl, mono- or polysubstituted by fluorine, chlorine, bromine or iodine,
d) phenyl,
e) phenyl, mono- or polysubstituted by
  1) fluorine, chlorine, bromine or iodine,
  2) nitro,
  3) cyano,
  4) $(C_1-C_4)$-alkyl,
  5) $(C_1-C_4)$-alkyl, mono- or polysubstituted by fluorine, chlorine, bromine or iodine,
  6) $(C_1-C_4)$-alkoxy,
  7) $(C_1-C_4)$-alkoxy, mono- or polysubstituted by fluorine, chlorine, bromine or iodine,
f) benzyl,
g) $(C_3-C_7)$-cycloalkyl,
h) alkenyl having 2 or 3 carbon atoms or
i) alkynyl having 2 or 3 carbon atoms, $R^2$ is
a) a hydrogen atom,
b) $(C_1-C_4)$-alkyl, c) phenyl,
d) phenyl-$(C_1-C_2)$-alkyl or
e) alkenyl having 2 to 3 carbon atoms, or $R^3$ is
a) a mono-, di- or trinuclear, unsaturated heterocyclic radical having 3 to 13 carbon atoms and 1 to 4 heteroatoms from the group consisting of oxygen, sulfur and nitrogen, of which at most one of the heteroatoms in the ring system is other than nitrogen, and is unsubstituted or mono- or polysubstituted by
  1) fluorine, chlorine, bromine or iodine,
  2) $(C_1-C_4)$-alkyl,
  3) $(C_1-C_4)$-alkyl, mono- or polysubstituted by fluorine, chlorine, bromine or iodine,
  4) $(C_1-C_4)$-alkoxy,
  5) $(C_1-C_4)$-alkoxy, mono- or polysubstituted by fluorine, chlorine, bromine or iodine,
  6) nitro,
  7) hydroxyl,
  8) carboxyl,
  9) carbamoyl or
  10) an oxo group,
b) a radical of the formula II

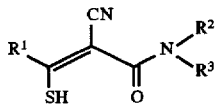

wherein $R^4$, $R^5$ and $R^6$ are each independently
  1) a hydrogen atom,
  2) $(C_1-C_4)$-alkyl,
  3) $(C_1-C_4)$-alkyl, mono- or polysubstituted by fluorine, chlorine, bromine or iodine,
  4) wherein $R^4$ is a hydrogen atom and $R^5$ and $R^6$, together with the phenyl ring of the formula II, form a naphthalene ring,
  5) wherein $R^4$ is a hydrogen atom and $R^5$ and $R^6$ form a methylenedioxy radical,
  6) $(C_1-C_4)$-alkoxy,
  7) $(C_1-C_4)$-alkoxy, mono- or polysubstituted by fluorine, chlorine, bromine or iodine,
  8) $(C_1-C_4)$-alkylmercapto,
  9) $(C_1-C_4)$-alkylmercapto, mono- or polysubstituted by fluorine, chlorine, bromine or iodine,
  10) fluorine, chlorine, bromine or iodine,
  11) nitro,
  12) cyano,
  13) hydroxyl,
  14) carboxyl,
  15) $(C_1-C_4)$-alkylsulfonyl,
  16) carbalkoxy, having 1 to 3 carbon atoms in the alkyl chain,
  17) benzoyl,
  18) benzoyl, mono- or polysubstituted by
    18.1 fluorine, chlorine, bromine or iodine,
    18.2 $(C_1-C_4)$-alkyl or
    18.3 $(C_1-C_4)$-alkoxy,
  19) phenyl,
  20) phenyl, mono- or polysubstituted by
    20.1 $(C_1-C_4)$-alkoxy,
    20.2 fluorine, chlorine, bromine or iodine or
    20.3 $(C_1-C_4)$-alkyl,
  21) phenoxy, or
  22) phenoxy, mono- or polysubstituted by $(C_1-C_3)$-alkoxy, mono- or polysubstituted by 22.1 fluorine, chlorine, bromine or iodine,
22.2 ($C_1$–$C_3$)-alkyl, mono- or polysubstituted by fluorine, chlorine, bromine or iodine, or
22.3 fluorine, chlorine, bromine or iodine, c) a radical of the formula III

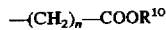   (III)

wherein $R^{10}$ is
1) a hydrogen atom or
2) ($C_1$–$C_4$)-alkyl and
n is an integer from 1 to 12, or d) $R^2$ and $R^3$, together with the nitrogen atom to which they are bonded, form a 4- to 7-membered ring, which is unsubstituted or substituted by carbonyl on the carbon atom adjacent to the nitrogen atom, or e) $R^2$ and $R^3$, together with the nitrogen atom to which they are bonded, form a 5- to 6-membered ring of the formula IV

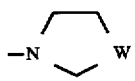   (IV)

wherein W is
1) —$CH_2$—,
2) —$CH_2$—$CH_2$—,
3)

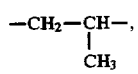

4)

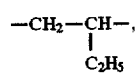

5)

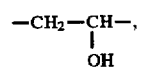

6) —$CH_2$—O— or
7) —$CH_2$—S—.

2. A method according to claim 1 wherein
$R^1$ is
a) a hydrogen atom,
b) ($C_1$–$C_6$)-alkyl,
c) ($C_1$–$C_4$)-alkyl, mono- or polysubstituted by fluorine, chlorine, bromine or iodine,
d) phenyl,
e) alkenyl having 2 or 3 carbon atoms or
f) ($C_3$–$C_4$)-cycloalkyl,
$R^2$ is
a) a hydrogen atom,
b) ($C_1$–$C_4$)-alkyl,
c) benzyl or
d) alkenyl having 2 to 3 carbon atoms,
$R^3$ is
a) pyridyl, mono- or polysubstituted by
1) a hydrogen atom,
2) fluorine, chlorine, bromine or iodine,
3) nitro,
4) ($C_1$–$C_3$)-alkyl or
5) ($C_1$–$C_3$)-alkoxy, b) a radical of the formula II in which $R^4$, $R^5$ and $R^6$ are each independently
1) a hydrogen atom,
2) ($C_1$–$C_3$)-alkyl,
3) ($C_1$–$C_3$)-alkyl, mono- or polysubstituted by fluorine, chlorine, bromine or iodine,
4) wherein $R^4$ is a hydrogen atom and $R^5$ and $R^6$ form a methylenedioxy radical,
5) ($C_1$–$C_3$)-alkoxy,
6) ($C_1$–$C_3$)-alkoxy, mono- or polysubstituted by fluorine, chlorine, bromine or iodine,
7) ($C_1$–$C_3$)-alkylmercapto,
8) ($C_1$–$C_3$)-alkylmercapto, mono- or polysubstituted by fluorine, chlorine, bromine or iodine,
9) fluorine, chlorine, bromine or iodine,
10) nitro,
11) cyano,
12) ($C_1$–$C_3$)-alkylsulfonyl,
13) benzoyl,
14) benzoyl, mono- or polysubstituted by
14.1 fluorine, chlorine, bromine or iodine,
14.2 ($C_1$–$C_3$)-alkyl or
14.3 ($C_1$–$C_3$)-alkoxy,
15) phenoxy, or
16) phenoxy, mono- or polysubstituted by
16.1 ($C_1$–$C_3$)-alkoxy, mono- or polysubstituted by fluorine, chlorine, bromine or iodine,
16.2 fluorine, chlorine, bromine or iodine,
16.3 ($C_1$–$C_3$)-alkyl, mono- or polysubstituted by fluorine, chlorine, bromine or iodine, c) a radical of the formula III in which $R^{10}$ is
1) a hydrogen atom,
2) ($C_1$–$C_4$)-alkyl and
n is an integer from 1 to 12, or d) $R^2$ and $R^3$, together with the nitrogen atom to which they are bonded, form a 4- to 7-membered ring which is substituted by carbonyl on the carbon atom adjacent to the nitrogen atom.

3. A method as in either claim 1 or claim 2, wherein
$R^1$ is ($C_1$–$C_6$)-alkyl,
$R^2$ is a hydrogen atom,
$R^3$ is
a) pyridyl, mono- or polysubstituted by fluorine, chlorine, bromine or iodine, or
b) a radical of the formula II in which $R^4$, $R^5$ and $R^6$ are each independently
1) a hydrogen atom or
2) ($C_1$–$C_3$)-alkyl,
3) ($C_1$–$C_3$)-alkyl, mono- or polysubstituted by fluorine, chlorine, bromine or iodine,
4) in which $R^4$ is a hydrogen atom and $R^5$ and $R^6$ form a methylenedioxy radical,
5) ($C_1$–$C_3$)-alkoxy,
6) ($C_1$–$C_3$)-alkoxy, mono- or polysubstituted by fluorine, chlorine, bromine or iodine,
7) fluorine, chlorine, bromine or iodine,
8) nitro,
9) benzoyl,
10) benzoyl, mono- or polysubstituted by
10.1 fluorine, chlorine, bromine or iodine,
10.2 ($C_1$–$C_3$)-alkyl or
10.3 ($C_1$–$C_3$)-alkoxy,
11) phenoxy or 12) phenoxy, mono- or polysubstituted by 12.1 $(C_1-C_3)$-alkoxy, mono- or polysubstituted by fluorine, chlorine, bromine or iodine, 12.2 fluorine, chlorine, bromine or iodine or 12.3 $(C_1-C_3)$-alkyl, mono- or polysubstituted by fluorine, chlorine, bromine or iodine.

4. A method according to claim 1 wherein the compound is 2-Cyano-3-mercapto-N-(4-trifluoromethylphenyl) crotonamide.

5. A method according to claim 1 wherein the compound is sodium 2-cyano-N-(4-trifluoromethylphenyl) crotonamide-3-thiolate.

\* \* \* \* \*